(12) United States Patent
Kaneko

(10) Patent No.: US 11,439,294 B2
(45) Date of Patent: Sep. 13, 2022

(54) INSERTION APPARATUS, ENDOSCOPE, AND CONNECTION STRUCTURE FOR CONNECTING EXTERIOR MEMBER AND CYLINDRICAL MEMBER

(71) Applicant: OLYMPUS CORPORATION, Tokyo (JP)

(72) Inventor: Mitsuru Kaneko, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 213 days.

(21) Appl. No.: 16/888,984

(22) Filed: Jun. 1, 2020

(65) Prior Publication Data

US 2020/0288949 A1 Sep. 17, 2020

Related U.S. Application Data

(63) Continuation of application No. PCT/JP2018/034476, filed on Sep. 18, 2018.

(30) Foreign Application Priority Data

Nov. 30, 2017 (JP) .............................. JP2017-230645

(51) Int. Cl.
*A61B 1/00* (2006.01)
*A61B 1/005* (2006.01)
(Continued)

(52) U.S. Cl.
CPC ........ *A61B 1/00124* (2013.01); *A61B 1/0056* (2013.01); *A61B 1/00105* (2013.01); *A61M 39/12* (2013.01); *G02B 23/24* (2013.01)

(58) Field of Classification Search
CPC ............ A61B 1/00105; A61B 1/00112; A61B 1/00121; A61B 1/00124; A61B 1/00128; A61B 1/00137
See application file for complete search history.

(56) References Cited

U.S. PATENT DOCUMENTS 5,301,061 A * 4/1994 Nakada .............. A61B 1/00105
359/511
6,106,457 A * 8/2000 Perkins .................. A61B 1/042
600/172
2012/0329312 A1 12/2012 Oue et al.

FOREIGN PATENT DOCUMENTS

CN 103337734 A 10/2013
EP 2594190 A1 5/2013
(Continued)

OTHER PUBLICATIONS

International Search Report dated Nov. 13, 2018 issued in PCT/JP2018/034476.

*Primary Examiner* — Aaron B Fairchild
(74) *Attorney, Agent, or Firm* — Scully, Scott, Murphy & Presser, P.C.

(57) ABSTRACT

An insertion apparatus includes: a bend preventing member having a first opening and a second opening; an exterior member connected to the bend preventing member in a state where the exterior member abuts against a second surface side, and a projection which is formed on the second surface circumferentially in a protruding manner toward the exterior member, the projection being elastically deformable such that the projection is inclined in an outside direction of the bend preventing member by making the projection abut against the exterior member.

11 Claims, 5 Drawing Sheets

(51) Int. Cl.
*A61M 39/12* (2006.01)
*G02B 23/24* (2006.01)

(56) References Cited

FOREIGN PATENT DOCUMENTS

| | | |
|---|---|---|
| JP | S51-158191 | 12/1976 |
| JP | S59-046933 A | 3/1984 |
| JP | H06-327618 A | 11/1994 |
| JP | H10-276972 A | 10/1998 |
| JP | 2010-035621 A | 2/2010 |
| JP | 2010-142254 A | 7/2010 |
| WO | WO 2012/077626 A1 | 6/2012 |

* cited by examiner

INSERTION APPARATUS, ENDOSCOPE, AND CONNECTION STRUCTURE FOR CONNECTING EXTERIOR MEMBER AND CYLINDRICAL MEMBER

CROSS REFERENCE TO RELATED APPLICATION

This application is a continuation application of PCT/JP2018/034476 filed on Sep. 18, 2018 and claims benefit of Japanese Application No. 2017-230645 filed in Japan on Nov. 30, 2017, the entire contents of which are incorporated herein by this reference.

BACKGROUND OF INVENTION

1. Field of the Invention

The present invention relates to an insertion apparatus which includes a cylindrical member having an outer peripheral surface formed in a tapered shape and an exterior member connected to the cylindrical member, an endoscope, and a connection structure for connecting the exterior member and the cylindrical member.

2. Description of the Related Art

Recently, an insertion apparatus such as an endoscope has been popularly used in a medical field and an industrial field.

A well-known structure of an endoscope includes: an insertion portion which is inserted into a subject; an operation portion which is connected to a proximal end of the insertion portion; a universal cord which extends from the operation portion; and a connector which is mounted on an extending end of the universal cord and is detachably connected to an external apparatus.

In such an endoscope, there has been a well-known structure where the insertion portion and the universal cord are connected to the operation portion by way of a known bend preventing member which is a cylindrical member.

As the connection structure which connects the bend preventing member to the operation portion, there has been a well-known technique or a structure where a screw mounted on the operation portion is threadedly engaged with a threaded hole which is a fixing portion formed on an inner peripheral surface of the bend preventing member by way of an opening formed in the bend preventing member on an operation portion side, and an exterior member of the operation portion is made to abut against a surface of the bend preventing member which has the opening on the operation portion side.

The configuration which connects the bend preventing member to the operation portion using the screw in this manner is disclosed in Japanese Patent Application Laid-Open Publication No. 2010-142254.

However, in the configuration where the exterior member of the operation portion is made to abut against the surface of the bend preventing member having the opening on the operation portion side by screw fixing, the opening is largely opened after an abutting operation and hence, there is a possibility that a fine gap is formed circumferentially between the surface and the exterior member. To prevent the formation of such a fine gap, it has been necessary to increase accuracy in forming these members and also it is necessary to pay an utmost care in assembling these members.

Accordingly, in Japanese Patent Application Laid-Open Publication No. 2010-142254, a configuration is disclosed where a bottom cover is mounted on a connecting portion between an exterior member of an operation portion and a bend preventing member, an outer peripheral surface of one end of the bottom cover is made to abut against an inner peripheral surface of the exterior member of the operation portion, and an inner peripheral surface of the other end of the bottom cover is made to abut against an outer peripheral surface of the bend preventing member. Accordingly, the configuration can prevent the above-mentioned gap from being exposed to the outside by the bottom cover.

SUMMARY OF THE INVENTION

According to an aspect of the present invention, there is provided an insertion apparatus which includes: a cylindrical member formed in a cylindrical shape, having a first opening formed in one end of the cylindrical member and a second opening formed in the other end of the cylindrical member and having a larger diameter than the first opening, and having an outer peripheral surface which connects a first surface having the first opening and a second surface having the second opening and is formed in a tapered shape; an exterior member connected to the cylindrical member in a state where the exterior member abuts against a second surface side of the cylindrical member; and a projection formed on the second surface circumferentially in a projecting manner toward the exterior member, the projection being elastically deformable such that the projection is inclined toward an outside in a radial direction of the cylindrical member by being made to abut against the exterior member.

According to another aspect of the present invention, there is provided an insertion apparatus which includes: a cylindrical member formed in a cylindrical shape, having a first opening formed in one end of the cylindrical member and a second opening formed in the other end of the cylindrical member and having a larger diameter than the first opening, and having an outer peripheral surface which connects a first surface having the first opening and a second surface having the second opening; an exterior member connected to the cylindrical member in a state where the exterior member abuts against a second surface side of the cylindrical member; and a projection formed on the second surface circumferentially in a projecting manner toward the exterior member, the projection formed such that a width of the projection in a radial direction is decreased in an outside direction as the projection extends in a direction that the projection is made to abut against the exterior member, and projection being elastically deformable such that the projection is inclined toward an outside in a radial direction of the cylindrical member.

According to still another aspect of the present invention, there is provided an endoscope which is formed of the insertion apparatus.

According to still another aspect of the present invention, there is provided a connection structure for connecting an exterior member and a cylindrical member, the connection structure including: a cylindrical member formed in a cylindrical shape, having a first opening formed in one end of the cylindrical member and a second opening formed in the other end of the cylindrical member and having a larger diameter than the first opening, and having an outer peripheral surface which connects a first surface having the first opening and a second surface having the second opening and is formed in a tapered shape; an exterior member connected to the cylindrical member in a state where the exterior member abuts against a second surface side of the cylindrical member; and a projection formed on the second surface circumferentially in a projecting manner toward the exterior member, the projection formed such that a width of the projection in a radial direction is decreased in an outside direction as the projection extends in a direction that the projection is made to abut against the exterior member, and projection being elastically deformable such that the projection is inclined toward an outside in a radial direction of the cylindrical member.

DETAILED DESCRIPTION OF THE PREFERRED EMBODIMENT

Hereinafter, an embodiment of the present invention is described with reference to drawings. Drawings are schematic views. Accordingly, it must be noted that a relationship between a thickness and a width of each member, a ratio between thicknesses of respective members and the like differ from the corresponding relationships of members of an actual insertion apparatus. Needless to say, portions of the insertion apparatus are described with different size relationship or different ratios between the drawings.

In the embodiment described hereinafter, the description is made by taking an endoscope as an example of an insertion apparatus.

Figure 1:
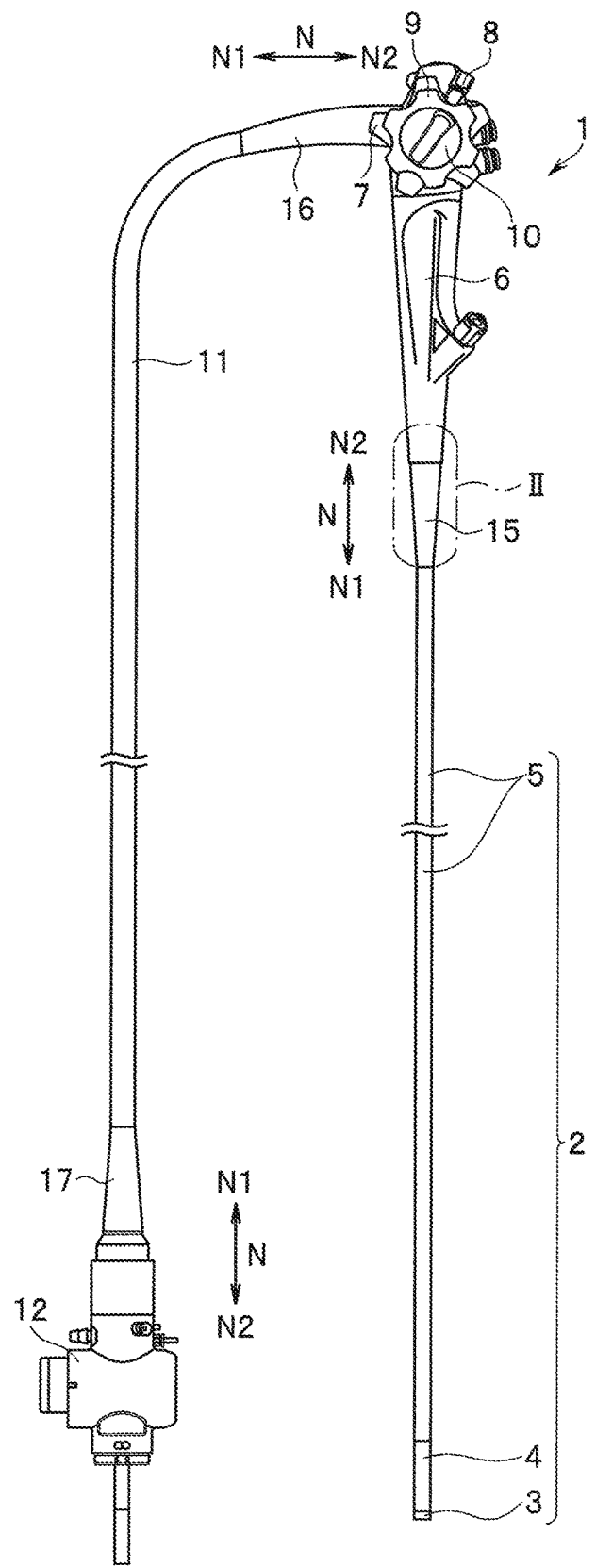
FIG. 1 is a view showing an external appearance of an endoscope according to an embodiment.

FIG. 1 is a view showing an external appearance of an endoscope according to the present embodiment.

As shown in FIG. 1, a main part of the endoscope 1 is formed of: an insertion portion 2 which has flexibility and is inserted into a subject; an operation portion 6 which is connected to a proximal end of the insertion portion 2 by way of a bend preventing member 15 which is a cylindrical member; a universal cord 11 which extends from the operation portion 6 by way of a bend preventing member 16 which is a cylindrical member, and a connector 12 which is connected to an extending end of the universal cord 11 by way of a bend preventing member 17.

The endoscope 1 is electrically connected to external apparatuses such as a controller and an illumination apparatus via the connector 12.

The operation portion 6 includes: a vertical bending operation knob 7 which bends a bending portion 4 (described later) of the insertion portion 2 in a vertical direction; and a lateral bending operation knob 9 which bends the bending portion 4 in a lateral direction.

The operation portion 6 further includes: a fixing lever 8 which fixes a rotary position of the vertical bending operation knob 7; and a fixing knob 10 which fixes a rotary position of the lateral bending operation knob 9.

The insertion portion 2 includes a distal end portion 3, the bending portion 4, and a flexible tube portion 5 which are arranged in this order from a distal end side, and is formed in an elongated shape.

The bending portion 4 is bent in a plurality of directions, for example, in four directions, that is, in the upward, downward, leftward, and rightward directions through operations on a hand side of the insertion portion 2, more specifically, rotary operations of the vertical bending operation knob 7 and the lateral bending operation knob 9 mounted on the operation portion 6. With such operations, the bending portion 4 can change an observation direction of an observation optical system not shown in the drawing which is mounted in the distal end portion 3, and can enhance inserting ability of the distal end portion 3 in a subject.

The flexible tube portion 5 is connected to a hand side of the bending portion 4, and has flexibility to an extent that the flexible tube portion 5 is bent in a passive manner.

Next, the connection structures for connecting the bend preventing members 15, 16 to the operation portion 6 and the connection structure for connecting the bend preventing member 17 to the connector 12 are described with reference to FIG. 2 to FIG. 7.

The connection structures for connecting the bend preventing members 15, 16 to the operation portion 6 and the connection structure for connecting the bend preventing member 17 to the connector 12 are described by taking the bend preventing member 15 as an example.

Figure 2:
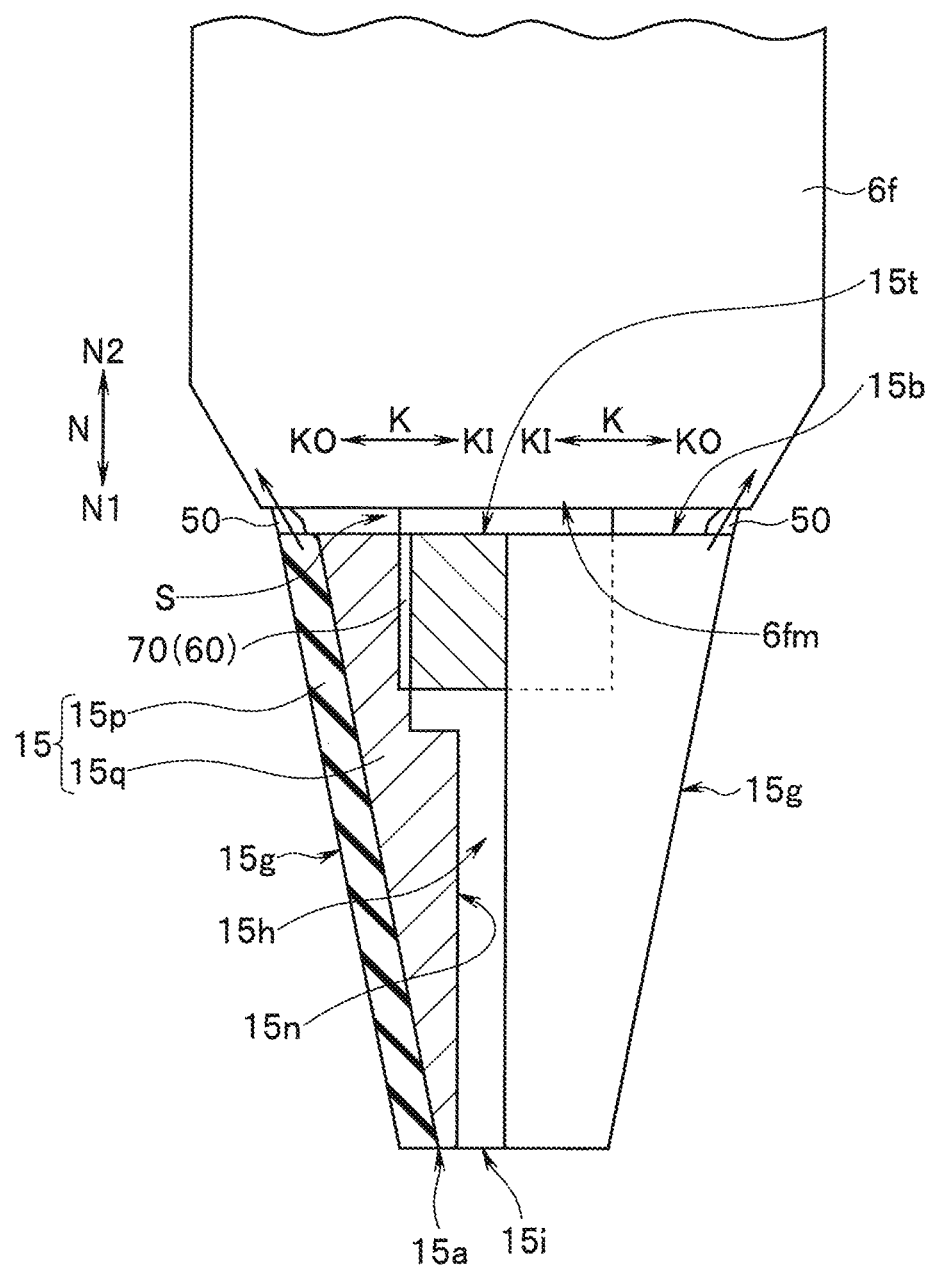
FIG. 2 is an enlarged cross-sectional view showing a part of a cylindrical member and a part of an exterior member surrounded by a line II in FIG. 1 with a half of the cylindrical member in cross-section.
Figure 3:
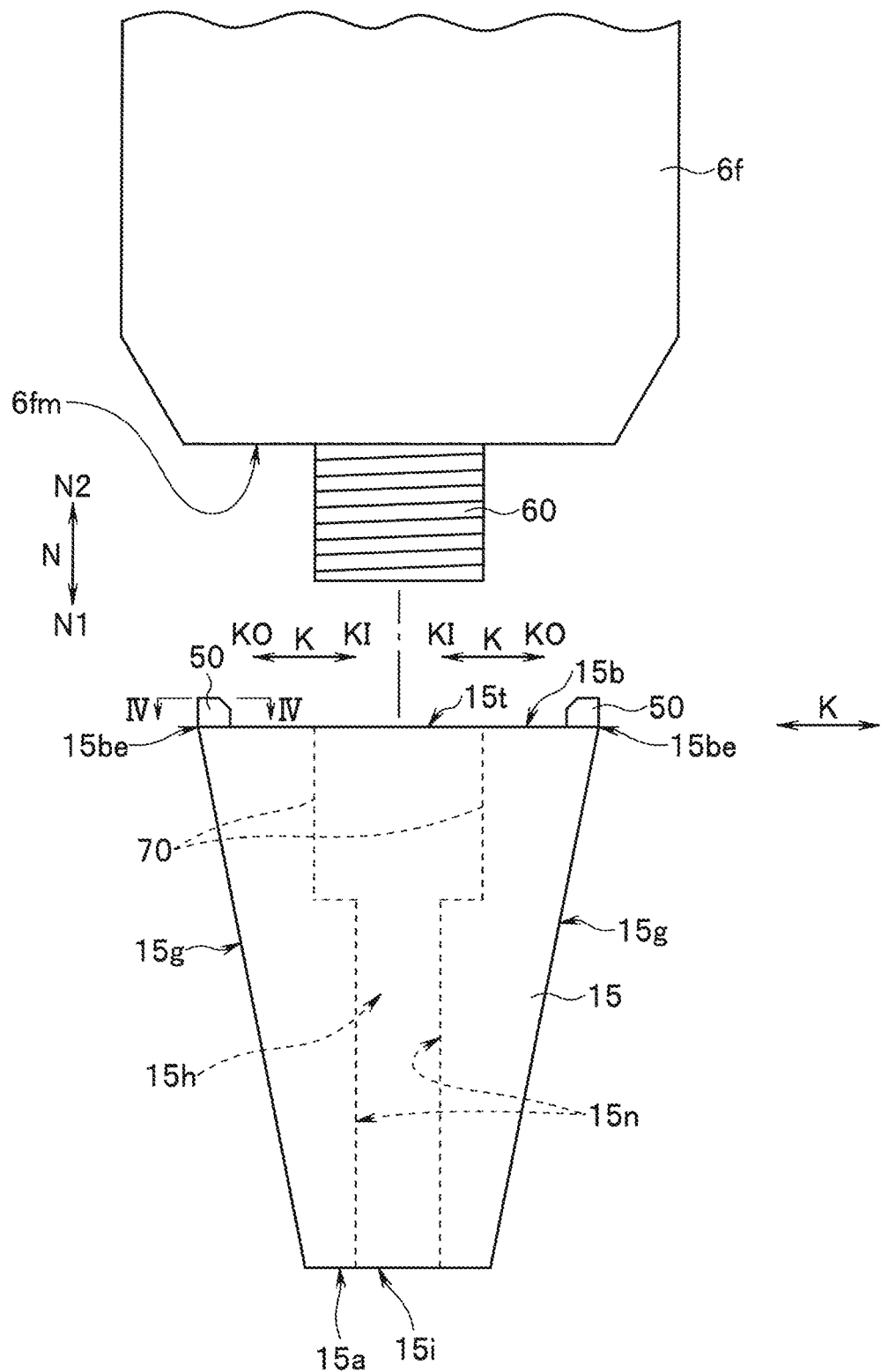
FIG. 3 is a view showing a state where the cylindrical member is removed from the exterior member in FIG. 2.

FIG. 2 is an enlarged cross-sectional view showing a part of a cylindrical member and a part of an exterior member surrounded by a line II in FIG. 1 with a half of the cylindrical member in cross-section, and FIG. 3 is a view showing a state where the cylindrical member is removed from the exterior member in FIG. 2.

Figure 4:
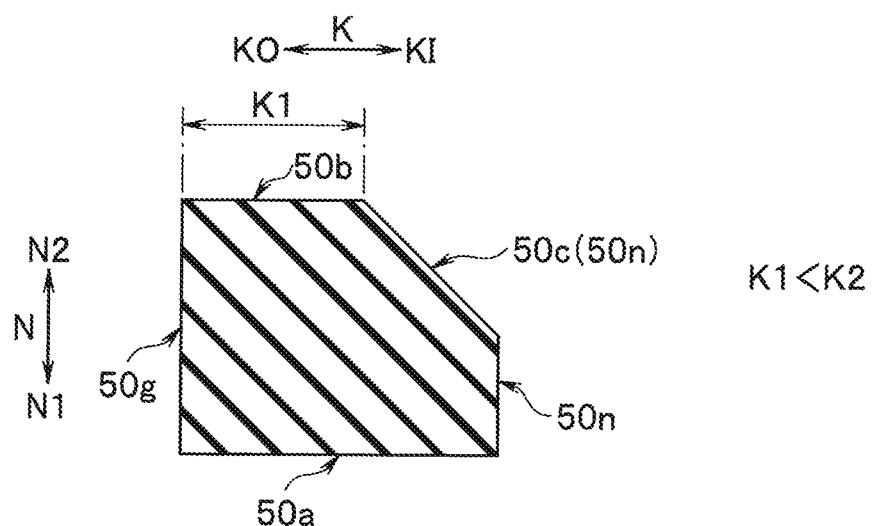
FIG. 4 is a cross-sectional view of a projection extending in a direction that the projection is made to abut against the exterior member taken along a line IV-IV in FIG. 3.
Figure 5:
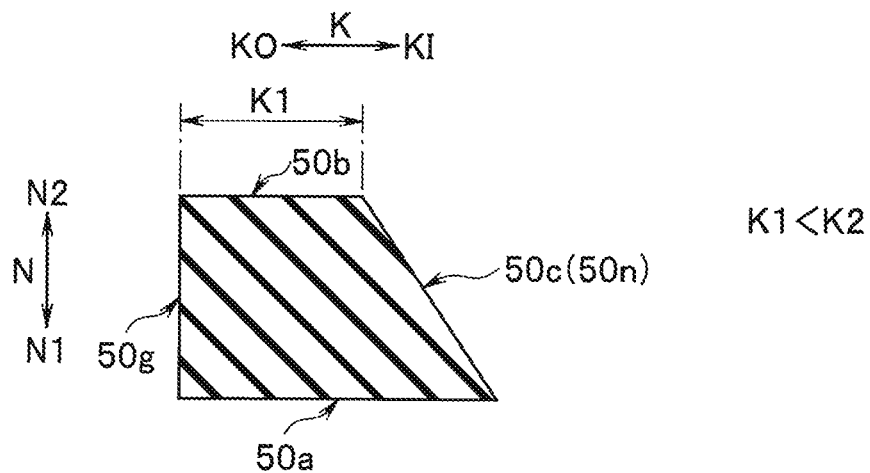
FIG. 5 is a cross-sectional view of a modification of the projection shown in FIG. 4 formed in a trapezoidal shape in cross section in the direction that the projection is made to abut against the exterior member.

FIG. 4 is a cross-sectional view of a projection in a direction that the projection is made to abut against the exterior member taken along a line IV-IV in FIG. 3, and FIG. 5 is a cross-sectional view of a modification of the projection shown in FIG. 4 formed in a trapezoidal shape in cross section in the direction that the projection is made to abut against the exterior member.

Figure 6:
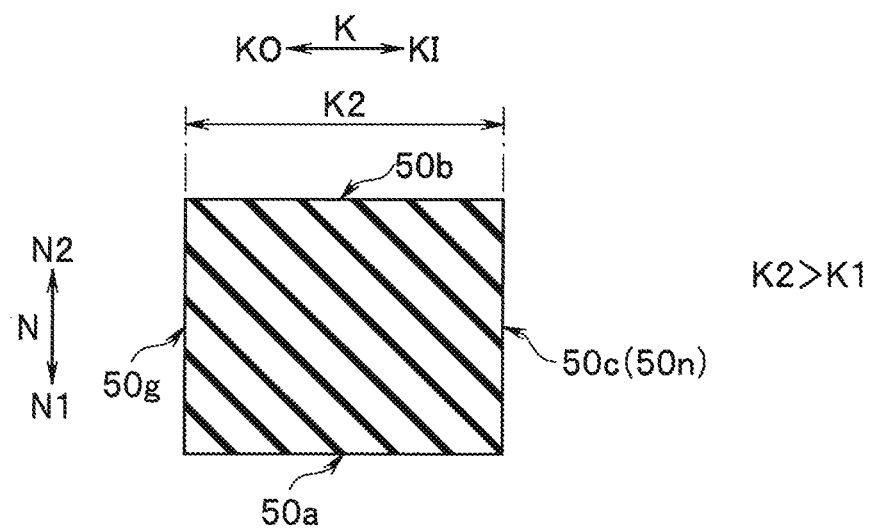
FIG. 6 is a cross-sectional view of a modification of the projection shown in FIG. 4 formed in a rectangular shape in cross section in the direction that the projection is made to abut against the exterior member.
Figure 7:
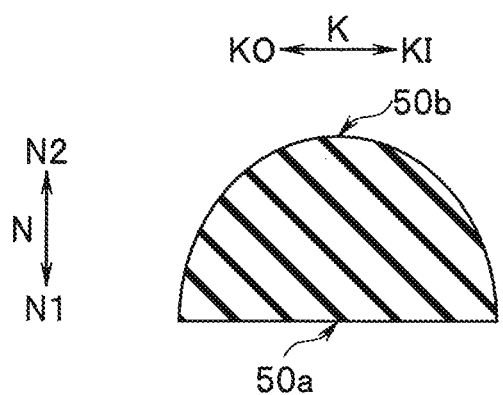
FIG. 7 is a cross-sectional view of a modification of the projection shown in FIG. 4 formed in a semicircular shape in cross section in the direction that the projection is made to abut against the exterior member.

FIG. 6 is a cross-sectional view of a modification of the projection shown in FIG. 4 formed in a rectangular shape in cross section in the direction that the projection is made to abut against the exterior member, and FIG. 7 is a cross-sectional view of a modification of the projection shown in FIG. 4 formed in a semicircular shape in cross section in the direction that the projection is made to abut against the exterior member.

As shown in FIG. 2 and FIG. 3, the bend preventing member 15 is configured such that an elastic member $15p$ made of rubber, for example, is integrally formed on an outer periphery of a rigid member $15q$ made of metal, for example. More specifically, the rigid member $15q$ is formed in a cylindrical shape in the elastic member $15p$ by insert molding along a longitudinal axis N of the bend preventing member 15.

The bend preventing member 15 has a first opening 15*i* in one end of the rigid member 15*q* along the longitudinal axis N, and a second opening 15*t* having a larger diameter than the first opening 15*i* on the other end of the rigid member 15*q* along the longitudinal axis N. A through hole 15*h* which connects the first opening 15*i* and the second opening 15*t* is formed in the rigid member 15*q* along the longitudinal axis N. A proximal end side of the flexible tube portion 5 of the insertion portion 2 is inserted into the through hole 15*h*, and the flexible tube portion 5 is fixed by known configuration.

In the bend preventing member 15, an outer peripheral surface 15*g* of the elastic member 15*p* which connects a first surface 15*a* having the first opening 15*i* and a second surface 15*b* having the second opening 15*t* along the longitudinal axis N is formed in a tapered shape.

More specifically, in the elastic member 15*p*, the outer peripheral surface 15*g* is formed in a tapered shape such that a diameter of the outer peripheral surface 15*g* is enlarged in an outer side direction KO with respect to a radial direction K as the outer peripheral surface 15*g* extends from the first surface 15*a* to the second surface 15*b*, along the longitudinal axis N.

With respect to the rigid member 15*q* of the bend preventing member 15, a female thread 70 is formed on an inner peripheral surface 15*n* formed by the through hole 15*h* on a second surface 15*b* side. The female thread 70 forms a fixing member for threadedly fixing the bend preventing member 15 to an exterior member 6*f* (described later) in a direction N2 that the bend preventing member 15 is made to abut against the exterior member 6*f* of the operation portion 6.

The operation portion 6 has the exterior member 6*f* which is connected to the bend preventing member 15. The exterior member 6*f* has: an abutting surface 6*fm* which oppositely faces the second surface 15*b* of the bend preventing member 15; and a male thread 60 which projects from the abutting surface 6*fm* in a direction N1 of the longitudinal axis N.

As shown in FIG. 2, when the bend preventing member 15 is connected to the exterior member 6*f*, the male thread 60 threadedly engages with the female thread 70 of the bend preventing member 15, and the abutting surface 6*fm* abuts against projections 50 (described later) of the bend preventing member 15.

The fine projections 50 are formed on the second surface 15*b* of the elastic member 15*p* of the bend preventing member 15 on an outer periphery of the second opening 15*t* in an integral manner with the elastic member 15*p*.

The projections 50 project toward the exterior member 6*f*, that is, in the direction N2 along the longitudinal axis N circumferentially to fill a gap S formed between the second surface 15*b* and the abutting surface 6*fm* when the bend preventing member 15 is connected to the exterior member 6*f*. Further, as shown in FIG. 2, a surface 50*b* of each projection 50 is made to abut against the abutting surface 6*fm* and hence, the projections 50 are elastically deformed (collapsed) in an inclined manner in the outside direction KO with respect to the radial direction K.

Since the projections 50 are integrally formed with the elastic member 15*p*, the gap between both members is filled when the exterior member 6*f* and the bend preventing member 15 are connected and it is thus unnecessary to additionally arrange a separate member such as a O-shaped ring in the gap between both members for filling the gap as in the case of the prior art. As a result, assembling property of the endoscope 1 is enhanced.

As shown in FIG. 4 and FIG. 5, a cross section of each projection 50 in the direction N2 is formed in an approximately pentagonal shape or an approximately trapezoidal shape.

More specifically, the projection 50 is formed in a shape where an inner peripheral surface 50*n* has an inclined surface 50*c* inclined in the outside direction KO with respect to the radial direction K as the projection 50 extends in the direction N2.

In other words, the projection 50 is formed in a shape where a width of the projection 50 with respect to the radial direction K is decreased in the outside direction KO as the projection 50 extends in the direction N2.

As shown in FIG. 3, the projection 50 is formed such that an outer peripheral surface 50*g* of the projection 50 rises up in the direction N2 from an outer peripheral edge 15*be* of the second surface 15*b* of the bend preventing member 15. In other words, the outer peripheral surface 50*g* is formed along the longitudinal axis N, and is formed substantially perpendicular to the outer peripheral edge 15*be*.

The reason why a cross-sectional shape of the projection 50 in the direction N2 is formed in an approximately pentagonal shape or an approximately trapezoidal shape is that when the cross-sectional shape of the projection 50 in the direction N2 is formed in a rectangular shape as shown in FIG. 6, a contact area of the surface 50*b* with an abutting surface 6*fm* is increased as shown in FIG. 4 to FIG. 6 (K2>K1) so that a resistance by the projection 50 at the time of threadedly engaging the male thread 60 with the female thread 70 is increased. Note that K1 is a width with respect to the radial direction K of the surface 50*b* of the projection 50 on a side where the projection 50 is brought into contact with the exterior member 6*f*, and K2 is a width with respect to the radial direction K of the surface 50*b* of the projection 50 on a side where the projection 50 is connected to the exterior member 6*f*.

Further, in the case where an area of the surface 50*a* of the projection 50 that rises up from the elastic member 15*p* is decreased, that is, in the case where the area of the surface 50*a* is set, for example, equal to an area of the surface 50*b* as shown in FIG. 5 and FIG. 6, there is a possibility that the surface 50*a* is sheared from the elastic member 15*p* when the male thread 60 is threadedly engaged with the female thread 70, which is another reason.

Accordingly, the cross section of the projection 50 in the direction N2 is formed in an approximately pentagonal shape or an approximately trapezoidal shape where an area of the surface 50*a* is larger than the area of the surface 50*b*.

To prevent shearing of the projection 50 and to minimize a contact area of the surface 50*b* with the abutting surface 6*fm*, it is considered that a cross-sectional shape of the projection 50 in the direction N2 is formed in a semicircular shape as shown in FIG. 7.

However, when such a semicircular shape is adopted, when the projection 50 collapses along with contacting of the projection 50 with the abutting surface 6*fm*, the outer peripheral surface 50*g* of the projection 50 is indented more in the inside direction KI with respect to the radial direction K than the outer peripheral surface 15*g* of the bend preventing member 15. Accordingly, such a shape is not desirable.

As described previously, as shown in FIG. 3, the projection 50 is formed such that the outer peripheral surface 50*g* rises up in the direction N2 from the outer peripheral edge 15*be* of the second surface 15*b* of the bend preventing member 15. This is because when the projection 50 is inclined and collapses in the outside direction KO, the outer peripheral surface 50*g* is positioned such that the outer peripheral surface 50g forms a smooth continuous surface with no unevenness with respect to the outer peripheral surface 15g of the bend preventing member 15.

Further, the projection 50 is formed with an elastic modulus smaller than an elastic modulus of the elastic member 15p of the bend preventing member 15 and an elastic modulus of the exterior member 6f. In other words, the projection 50 is formed softer than the elastic member 15p and the exterior member 6f.

Other connection structure between the bend preventing member 15 and the exterior member 6f are equal to the corresponding configurations of the prior art.

As will be appreciated from the foregoing, in the present embodiment, the case is described where the projection 50 is formed on the second surface 15b of the bend preventing member 15 in a state where the projection 50 projects toward the exterior member 6f circumferentially, and the cross section of the projection 50 in the direction N2 in which the inner peripheral surface 50n has the inclined surface 50c inclined in the outside direction KO with respect to the radial direction K in the direction N2 is formed in an approximately pentagonal shape or an approximately trapezoidal shape.

With such a configuration, in connecting the bend preventing member 15 to the exterior member 6f, when the male thread 60 is threadedly engaged with the female thread 70, due to a face pressure generated by contacting of the surface 50b of the projection 50 with the abutting surface 6fm, the projection 50 is elastically deformed in the outside direction KO with respect to the radial direction K.

Accordingly, an influence of a spiral angle of the male thread 60 threadedly engaged with the female thread 70 can be absorbed by the deformation of the projection 50 and hence, it is possible to bring the surface 50b of the projection 50 into complete close contact with the abutting surface 6fm. As a result, it is possible to fill the gap S formed between the second surface 15b and the abutting surface 6fm with the collapsed projection 50 with certainty.

Further, since the cross section of the projection 50 is formed in an approximately pentagonal shape or an approximately trapezoidal shape, the surface 50b is formed smaller than when the cross section of the projection 50 has a rectangular shape. Accordingly, it is possible to prevent the increase of a resistance generated by the projection 50 when the male thread 60 is threadedly engaged with the female thread 70.

In the above-mentioned embodiment, the case is described where an elastic modulus of the projection 50 is smaller than an elastic modulus of the elastic member 15p of the bend preventing member 15 and an elastic modulus of the exterior member 6f.

With such a configuration, it is possible to accelerate the deformation of the projection 50 formed softer than the elastic member 15p and the exterior member 6f after the bend preventing member 15 is connected to the exterior member 6f while holding a function of the bend preventing member 15 itself. Accordingly, it is possible to bring the surface 50b of the projection 50 into complete close contact with the abutting surface 6fm. As a result, it is possible to completely fill the gap S formed between the second surface 15b and the abutting surface 6fm with the collapsed projection 50 with certainty.

Further, in the above-mentioned embodiment, as shown in FIG. 3, the case is described where the projection 50 is formed such that the outer peripheral surface 50g rises up in the direction N2 from the outer peripheral edge 15be of the second surface 15b of the bend preventing member 15.

With such a configuration, when the projection 50 is inclined and collapses in the outside direction KO after the bend preventing member 15 is connected to the exterior member 6f, the outer peripheral surface 50g is positioned so as to form a smooth continuous surface with no unevenness with respect to the outer peripheral surface 15g of the bend preventing member 15, which enhances the external appearance of the endoscope 1 and, further, cleaning/disinfecting of a portion where the projection 50 is formed.

As has been described heretofore, it is possible to provide the endoscope 1 having the configuration where the gap S formed at the time of connecting the bend preventing member 15 to the exterior member 6f can be filled with the projections 50 with a simple structure without forming a stepped portion.

In the above-mentioned embodiment, the connection structure for connecting the bend preventing member 15 to the exterior member 6f of the operation portion 6 is described as an example. However, the present invention is not limited to such a configuration. Needless to say, the present invention is applicable to a connection structure for connecting the bend preventing member 16 to the exterior member 6f and a connection structure for connecting the bend preventing member 17 to the connector 12. In other words, the bend preventing member 16 and the bend preventing member 17 also have the same connection structure as the bend preventing member 15.

In the present embodiment, the bend preventing member 15, 16 are exemplified as the cylindrical member, and the exterior member 6f of the operation portion 6 is exemplified as the exterior member. However, the present invention is not limited to such a configuration. The cylindrical member may be a different member provided that the member has a tapered surface on an outer peripheral surface and is formed in a cylindrical shape. The exterior member may also be an exterior member other than the operation portion.

The insertion apparatus is described by exemplifying the endoscope. However, the present invention is not limited to such an endoscope. Needless to say, the present invention is applicable to other insertion apparatuses such as a treatment instrument.

What is claimed is:

1. An insertion apparatus comprising:
   a tubular member formed in a tapered shape, the tubular member having a through hole with a first opening formed at one end of the through hole and a second opening formed at another end of the through hole, the second opening having a larger diameter than the first opening, and the tubular member having an outer tapered peripheral surface connecting a first surface having the first opening and a second surface having the second opening;
   an exterior member connected to the tubular member in a state where the exterior member abuts against a projection on the second surface of the tubular member; and
   the projection circumferentially formed on the second surface to project toward the exterior member, the projection being elastically deformable such that the projection is inclined radially outward from a central longitudinal axis of the tubular member when the projection is made to abut against the exterior member.

2. The insertion apparatus according to claim 1, wherein an inner peripheral surface of the projection has an inclined surface inclined radially outward from the central longitudinal axis of the tubular member toward the exterior member with respect to a direction that the projection is made to abut against the exterior member.

3. The insertion apparatus according to claim 2, wherein a cross section of the projection in a direction that the projection is made to abut against the exterior member has an approximately trapezoidal shape or an approximately pentagonal shape.

4. The insertion apparatus according to claim 1, wherein an outer peripheral surface of the projection is formed so as to extend in a direction that the projection is made to abut against the exterior member from an outer peripheral edge of the second surface of the tubular member.

5. The insertion apparatus according to claim 1, wherein an elastic modulus of the projection is smaller than each of an elastic modulus of the tubular member and an elastic modulus of the exterior member.

6. The insertion apparatus according to claim 1, wherein the through hole has a female thread which is threadedly fixed to a mating male thread on the exterior member in a direction that the tubular member is made to abut against the exterior member.

7. The insertion apparatus according to claim 1, wherein the projection is formed in a protruding manner along the central longitudinal axis of the tubular member.

8. The insertion apparatus according to claim 1, wherein a portion of the projection is disposed in a gap formed between the second surface of the tubular member and the exterior member.

9. An endoscope according to claim 1, wherein the insertion apparatus is an endoscope.

10. An insertion apparatus comprising:
a tubular member formed in a tapered shape, the tubular member having a through hole with a first opening formed at one end of the through hole and a second opening formed at another end of the through hole, the second opening and having a larger diameter than the first opening, and the tubular member having an outer tapered peripheral surface connecting a first surface having the first opening and a second surface having the second opening;

an exterior member connected to the tubular member in a state where the exterior member abuts against a ring-shaped projection on the second surface of the tubular member; and the ring-shaped projection circumferentially formed on the second surface to project toward the exterior member, the projection formed such that a distance between an inner diameter and an outer diameter of the projection decreases as the projection extends away from the second surface, and the projection being elastically deformable such that the projection is inclined radially outward from a central longitudinal axis of the tubular member when the projection is made to abut against the exterior member.

11. A connection structure for connecting an exterior member and a tubular member, the connection structure comprising:
the tubular member formed in a tapered shape, the tubular member having a through hole with a first opening formed at one end of the through hole and a second opening formed at another end of the through hole, the second opening having a larger diameter than the first opening, and the tubular member having an outer tapered peripheral surface connecting a first surface having the first opening and a second surface having the second opening and is formed in a tapered shape;

the exterior member connected to the tubular member in a state where the exterior member abuts against a ring-shaped projection on the second surface of the tubular member; and the ring-shaped projection circumferentially formed on the second surface to project toward the exterior member, the projection formed such that a distance between an inner diameter and an outer diameter of the projection decreases as the projection extends away from the second surface, and the projection being elastically deformable such that the projection is inclined radially outward from a central longitudinal axis of the tubular member when the projection is made to abut against the exterior member.

* * * * *